United States Patent [19]

Durand

[11] Patent Number: 5,458,872
[45] Date of Patent: Oct. 17, 1995

[54] METHOD FOR THE PROTECTION OF DIHYDROXYACETONE, A DIHYDROXYACETONE PROTECTED BY THIS METHOD, AND A COSMETIC PRODUCT CONTAINING SUCH A PROTECTED DIHYDROXYACETONE

[76] Inventor: Muriel Durand, 28, rue d'entraigues, 37000 Tours, France

[21] Appl. No.: 860,504

[22] PCT Filed: Jan. 29, 1991

[86] PCT No.: PCT/FR91/00053

§ 371 Date: Jun. 17, 1992

§ 102(e) Date: Jun. 17, 1992

[87] PCT Pub. No.: WO91/12222

PCT Pub. Date: Aug. 22, 1991

[30] Foreign Application Priority Data

Jan. 30, 1990 [FR] France ................................. 90 01070

[51] Int. Cl.$^6$ ................................................... A61K 7/42
[52] U.S. Cl. .................... 424/59; 424/490; 424/494; 424/497; 424/495; 424/498; 514/675
[58] Field of Search .............................. 424/59, 489, 490, 424/495, 494, 497, 498; 514/675

[56] References Cited

U.S. PATENT DOCUMENTS

| | | | |
|---|---|---|---|
| 4,434,154 | 2/1984 | Mc Shane | 424/60 |
| 4,855,090 | 8/1989 | Wallach | 264/4.1 |
| 4,911,928 | 3/1990 | Wallach | 424/450 |
| 5,093,107 | 3/1992 | Matravers | 424/59 |

FOREIGN PATENT DOCUMENTS 2085208  12/1971  France .

OTHER PUBLICATIONS

Derwent; WPI; AN–90–099893; 1989.
Hawley's Condensed Chemical Dictionary elventh edition; 1987; selected pages.
Beilstein: "Handbuch Der Organischen Chemie", Edition 4, vol. 1, 1918, by Julius Springer, p. 846, paragraph 6.
Chemical Abstracts, "Study on dihydroxyacetone preservation as a function of formulation", vol. 100, No. 8 of Feb. 20, 1984 by M. F. Bobin et al., p. 318, abstract 56724q.
Chemical Abstracts, "Stabilized preparation to tan the skin", vol. 72, No. 20, of May 18, 1970 by K. Hronsky, p. 223, abstract 10363b.
"Composition for Artificial Sun–Tan", *World Patent Index Lates Database*, Accession No. 83–825600, of week 47, sections D21,E19, 1983, by I. M. Erns et al.
*Seifen–ole–Fette–Wachse*, vol. 104, No. 9, Jun. 1978, p. 247, col. 2, lines 1–30.

*Primary Examiner*—José G. Dees
*Assistant Examiner*—Samuel Barts
*Attorney, Agent, or Firm*—Young & Thompson

[57] ABSTRACT

A method for protecting and stabilizing dihydroxyacetone (DHA) is described. The method is characterized in that at least a part of the dihydroxyacetone is enclosed in dimer form in a watertight composition which releases the dihydroxyacetone when applied. The protected and stabilized DHA composition has application in the cosmetics industry.

16 Claims, No Drawings

METHOD FOR THE PROTECTION OF DIHYDROXYACETONE, A DIHYDROXYACETONE PROTECTED BY THIS METHOD, AND A COSMETIC PRODUCT CONTAINING SUCH A PROTECTED DIHYDROXYACETONE

FIELD OF THE INVENTION

The present invention relates to dihydroxyacetone (DHA), and particularly to its cosmetic applications.

BACKGROUND OF THE INVENTION

The dihydroxyacetone has been used for many years in cosmetology for its skin pigmentation properties and has become a tanning agent used in what is usually called suntan creams.

Such a use of the dihydroxyacetone is faced with many difficulties due to its solubility in water, its oxidizing capacity, its weakness when subjected to heat, the instability of its pH, its sensitivity to microbial and bacterial agents, etc. These difficulties require using the product containing dihydroxyacetone very quickly after its preparation, the portion of dihydroxyacetone which remains active diminishing very rapidly with time. Moreover, the product has to be stored in optimum conditions of temperature and hygrometry in order to avoid the decomposition and/or dehydration of the aqueous solution of dihydroxyacetone.

In order to facilitate the use of dihydroxyacetone in the cosmetology industry, it is therefore necessary to remedy at least some of these disadvantages. The works carried out in this respect have resulted into the present invention.

SUMMARY OF THE INVENTION

To this effect, the invention relates to a method for the protection and stabilization of the dihydroxyacetone (DHA), characterized in that a portion at least of the dihydroxyacetone in the dimer form imbedded in a watertight composition which releases the dihydroxyacetone when applied.

The watertight composition protects the DHA from water and oxidation and forms an envelope ensuring a certain thermal insulation.

According to a preferred embodiment of the method of this invention, the watertight composition is soluble in a solvent.

Preferably, said watertight composition contains a mixture of polymers insoluble in water such as: cellulose acetophthalate, vinylidene polychloride, styrene-acrylonitrile copolymers, copolymers of dimethylaminoethylmethacrylate and other neutral esters of methacrylic acid, cellulose acetate, nitrocellulose, ethylhydroxyethyl cellulose and ethyl cellulose.

Advantageously, the watertight composition contains ethyl cellulose in a concentration of 0,1% to 10%, preferably of about 2%, with respect to the weight of DHA.

DETAILED DESCRIPTION OF THE INVENTION

In order to facilitate the release of DHA when applied on the skin, one has to ensure that the watertight composition contains oily fats having a set fusion point such as a mixture of monoglycerides, diglycerides or triglycerides of saturated or unsaturated fatty acids having a chain with a length between $C_9$ and $C_{22}$, preferably between $C_{12}$ and $C_{18}$, and one controls the fusion point and the hardness by adding hydrocarbons derived from petroleum, from silicones and derivatives thereof, from mineral, vegetable or animal waxes and/or from fatty alcohols, from their long chain esters and from saturated or unsaturated fatty acids, for example lauric, myristic, palmitic, oleic or stearic acid, and particularly stearic acid in a concentration of 1% to 15%, preferably of about 7%, with respect to the weight of DHA.

Advantageously, in order to stabilize the pH in a zone between acid and neutral inside of and in the immediate vicinity of the watertight composition, the invention provides that the composition contains an organic acid or one of its salts such as acids-phenols, acids-alcohols, or a precursor of such an acid in the form of lactone, particularly the glucuno-delta-lactone in a concentration of 0,01% to 2%, and preferably of about 0,15% with respect to the weight of DHA.

According to a preferred embodiment of the method according to the invention, and to avoid the bacterial degradation of DHA, one sees that said watertight composition contains a bacteriostatic and/or a bactericide and/or a fungicidal agent compatible with the use in cosmetology, such as the derivatives of isothiazolone, the formaldehyde generating products, the organic and mineral derivatives of mercury, bromine, chlorine, the acids, the alcohols, the phenols and derivatives thereof, particularly the derivatives of parahydroxybenzoic acid, of its esters, of its salts or of its solution in phenoxyethanol, in a concentration of 0,05% to 0,5%, preferably of about 0,15%, with respect to the weight of DHA.

According to the invention, the watertight composition is applied in a single application or in several applications containing each at least some of the components of said watertight composition, by a granulation, pelliculation or encapsulation operation by a fluidized bed or by paring in a turbine. These methods are such that they allow a lesser portion of the DHA to remain in a monomer form immediately usable from the cosmetologic viewpoint.

The invention relates also to the intermediate industrial product, in the cosmetologic industry, formed by the DHA protected and stabilized by the hereabove method, as well as the cosmetologic products containing this intermediate product.

EXAMPLE

By way of example, the composition of two protection layers applied according to the method of the invention to 1 kg of DHA will be described hereafter. The percentages mentioned are by weight.

| 1st layer | | |
| --- | --- | --- |
| Ethyl cellulose | (sealing agent) | 1,25% |
| Stearic acid | controlled sealing, | 4,00% |
| Triglycerides | fusion and crushing agents, cosmetic softener | 5,00% |

A plastifier of the ethylcellulose dissolved in alcohol or methylene choride.

| 2nd layer | | |
| --- | --- | --- |
| glucuno-delta-lactone | (pH stabilizer) | 0,10% |
| stearic acid | (as in layer 1) | 2,00% |
| triglycerides | (as in layer 1) | 20,50% |
| hydrophobic silica | (tightness, control of fusion point) | 0,11% |
| mixture of esters of parahydroxybenzoic acid dissolved in alcohol or methylene choride. | (antibacterial) | 0,10% |

The DHA thus protected has turned out to be without the faults of the non protected DHA, thereby allowing a reliable, large scale and stable application in the cosmetologic industry.

I claim:

1. Method for the protection and stabilization of dihydroxyacetone (DHA), comprising encapsulating particles of dihydroxyacetone in a watertight composition comprising at least one water-insoluble polymer, at least a portion of the encapsulated dihydroxyacetone being in the dimer form.

2. A method according to claim 1, wherein the watertight composition is soluble in a non-aqueous solvent.

3. A method according to claim 1, wherein said watertight composition contains a mixture of polymers insoluble in water, selected from the group consisting of cellulose acetophthalate, vinylidene polychloride, styrene-acrylonitrile copolymers, copolymers of dimethylaminoethylmethacrylate and other neutral esters of methacrylic acid, cellulose acetate, nitrocellulose, ethylhydroxyethyl cellulose and ethyl cellulose.

4. A method according to claim 3, wherein the watertight composition contains ethyl cellulose in a concentration of 0.1% to 10%, with respect to the weight of DHA.

5. A method according to claim 1, wherein the watertight composition contains oily fats having a set fusion point in the form of a mixture of monoglycerides, diglycerides and triglycerides of fatty acids having a chain length between $C_9$ and $C_{22}$, and wherein the fusion point and the hardness are controlled by adding hydrocarbons in a concentration of 1% to 15%, with respect to the weight of DHA.

6. A method according to claim 1, wherein the watertight composition contains an organic acid or one of its salts in a concentration of 0.01% to 2% with respect to the weight of DHA.

7. A method according to claim 1, wherein said watertight composition contains at least one of a bacteriostatic, a bactericide and a fungicidal agent in a concentration of 0.05% to 0.5% with respect to the weight of DHA.

8. A method according to claim 1, wherein the watertight composition is applied to the dihydroxyacetone by a granulation, pelliculation or encapsulation operation by a fluidized bed or by paring in a turbine.

9. A dihydroxyacetone composition protected and stabilized by the method according to claim 1, comprising dihydroxyacetone embedded at least in part in the dimeric form in said watertight composition, said watertight composition being in the form of one or several embedding layers.

10. Dihydroxyacetone according to claim 9, wherein the watertight composition is soluble in a non-aqueous solvent so as to maintain the dimeric DHA in a crystalline form.

11. Dihydroxyacetone according to claim 9, wherein said watertight composition contains a mixture of polymers insoluble in water selected from the group consisting of cellulose acetophthalate, vinylidene polychloride, styrene-acrylonitrile copolymers, copolymers of dimethylaminoethylmethacrylate and other neutral esters of methacrylic acid, cellulose acetate, nitrocellulose, ethylhydroxyethyl cellulose and ethyl cellulose.

12. Dihydroxyacetone according to claim 11, wherein the watertight composition contains ethyl cellulose in a concentration of 0.1% to 10%, with respect to the weight of DHA.

13. Dihydroxyacetone according to claim 9, wherein the watertight composition contains oily fats having a set fusion point in the form of a mixture of monoglycerides, diglycerides and triglycerides of fatty acids having a chain length between $C_9$ and $C_{22}$, and wherein the fusion point and the hardness are controlled by adding hydrocarbons in a concentration of 1% to 15%, with respect to the weight of DHA.

14. Dihydroxyacetone according to claim 9, wherein the watertight composition contains an organic acid or one of its salts in a concentration of 0.01% to 2% with respect to the weight of DHA.

15. Dihydroxyacetone according to claim 9, wherein said watertight composition contains at least one of a bacteriostatic, a bactericide and a fungicidal agent in a concentration of 0.05% to 0.5% with respect to the weight of DHA.

16. A cosmetologic product, characterized in that it contains dihydroxyacetone according to claim 9 in admixture with a cosmetologically acceptable carrier.

* * * * *